(12) United States Patent
Hradetzky et al.

(10) Patent No.: US 9,731,306 B2
(45) Date of Patent: Aug. 15, 2017

(54) ELECTROSPRAY DEVICE

(71) Applicants: UNIVERSITAT BERN, Bern (CH); FACHHOCHSCHULE NORDWESTSCHWEIZ FHNW, Brugg (CH)

(72) Inventors: David Hradetzky, Merdingen (DE); Erik Schkommodau, Liestal (CH); Stephan Bohringer, Efringen-Kirchen (DE); Amiq Gazdhar, Bern (CH); Thomas Geiser, Hinterkappelen (CH)

(73) Assignees: FACHHOCHSCHULE NORDWESTSCHWEIZ FHNW, Brugg (CH); UNIVERSITAT BERN, Bern (CH)

( * ) Notice: Subject to any disclaimer, the term of this patent is extended or adjusted under 35 U.S.C. 154(b) by 43 days.

(21) Appl. No.: 14/424,446

(22) PCT Filed: Aug. 28, 2013

(86) PCT No.: PCT/EP2013/067849
§ 371 (c)(1),
(2) Date: Feb. 27, 2015

(87) PCT Pub. No.: WO2014/033186
PCT Pub. Date: Mar. 6, 2014

(65) Prior Publication Data
US 2015/0251201 A1    Sep. 10, 2015

(30) Foreign Application Priority Data
Aug. 28, 2012  (EP) .................................. 12181986

(51) Int. Cl.
*B05B 5/00*  (2006.01)
*B05B 5/053*  (2006.01)
(Continued)

(52) U.S. Cl.
CPC .......... *B05B 5/0533* (2013.01); *A61M 11/00* (2013.01); *A61M 15/02* (2013.01); *B05B 5/0255* (2013.01);
(Continued)

(58) Field of Classification Search
CPC ..... B05B 5/0533; B05B 5/0255; B05B 5/087; B05B 5/1691; A61M 11/00; A61M 15/02;
(Continued)

(56) References Cited

U.S. PATENT DOCUMENTS

| 6,252,129 B1 * | 6/2001 | Coffee | A61F 13/00085 239/697 |
| 6,860,434 B2 * | 3/2005 | Ahn | B01J 2/02 239/690 |

(Continued)

FOREIGN PATENT DOCUMENTS

| WO | WO 98/03267 | 1/1998 |
| WO | WO2004/078244 | 9/2004 |
| WO | WO 2007/011866 | 1/2007 |

OTHER PUBLICATIONS

A. Gazdhar, P. Fachinger, C. van Leer, J. Pierog, M. Gugger, R. Friis, R. A. Schmid, and T. Geiser, "Gene transfer of hepatocyte growth factor by electroporation reduces bleomycin-induced lung fibrosis," Am J Physiol Lung Cell Mol Physiol, vol. 292 pp. L529-L536 Feb. 2007.
(Continued)

*Primary Examiner* — Steven J Ganey
(74) *Attorney, Agent, or Firm* — JMB Davis Ben-David

(57) ABSTRACT

The invention related to a device (1) for spraying charged droplets of a liquid towards a target along a spraying direction, comprising: a reservoir (10) for storing the liquid (L), a first electrode (100) being arranged at an outlet (11) of said reservoir (10), a second electrode (200) forming a
(Continued)

counter electrode to the first electrode (100) for accelerating said droplets (D) along the spraying direction (S), and a housing (30) holding the reservoir (10) as well as said electrodes (100, 200).

24 Claims, 10 Drawing Sheets

(51) Int. Cl.
    *A61M 11/00* (2006.01)
    *A61M 15/02* (2006.01)
    *B05B 5/025* (2006.01)
    *B05B 5/08* (2006.01)
    *B05B 5/16* (2006.01)
    *A61M 35/00* (2006.01)

(52) U.S. Cl.
    CPC ............ *B05B 5/087* (2013.01); *B05B 5/1691* (2013.01); *A61M 35/003* (2013.01); *A61M 2202/04* (2013.01); *A61M 2210/1039* (2013.01)

(58) Field of Classification Search
    CPC ............ A61M 35/003; A61M 2202/04; A61M 2210/1039
    USPC ................. 239/690, 697, 589, 602, DIG. 12, 239/DIG. 19; 118/621
    See application file for complete search history.

(56) References Cited

U.S. PATENT DOCUMENTS

| | | | | |
|---|---|---|---|---|
| 2001/0032897 | A1* | 10/2001 | Iwata | B05B 5/0531 239/690 |
| 2007/0048452 | A1 | 3/2007 | Feng et al. | |
| 2009/0088700 | A1 | 4/2009 | Imbayashi | |
| 2010/0155496 | A1* | 6/2010 | Stark | B05B 5/0255 239/690 |

OTHER PUBLICATIONS

D. Soden, M. Sadadcharam, J. Piggott, A. Morrissey, C. G. Collins, and G. C. O'Sullivan, "An endoscopic syqtem for gene & drug delivery directly to intraluminal tissue," in 11$^{TH}$ Mediterranean Conference on Medical and Biomedical Engineering and Computing 2007. vol. 16, R. Magjarevic, Ed.: Springer Berlin Heidelberg, 2007, pp. 628-628.

Y. Okubo, K. Ikemoto, K. Koike, C. Tsutsui, I. Sakata, O. Takei, A. Adachi, and T. Sakai, "DNA Introduction into living cells by water droplet impact with an electrospray process," Angewandte Chemie, vol. 120, pp. 1451-1453, 2008.

D.-R. Chen, C. Wendt, and D. Y. H. Pui, "A novel approach for introducing bio-materials into cells," Journal of Nanopartical Research, vol. 2, pp. 133-139, 2000. (Abstract Only).

* cited by examiner

ELECTROSPRAY DEVICE

CROSS-REFERENCE TO RELATED APPLICATIONS

This is the U.S. National Stage of International Application No. PCT/EP2013/067849, filed Aug. 28, 2013, which was published in English under PCT Article 21(2), which in turn claims the benefit of European Patent Application No. 12181986.6, filed Aug. 28, 2012.

The invention relates to a device for spraying charged droplets of a liquid towards a target along a spraying direction, particularly so as to deliver said liquid or a substance contained therein into a cell or a plurality of cells forming said target. I.e. the respective cell membrane is particularly overcome for delivering said liquid/substance into the respective cell (without destroying the cell).

Idiopathic pulmonary fibrosis (IPF) is a devastating disease affecting the distal lung. It is suggested that the failure of the alveolar epithelium to heal after micro-injuries triggers complex biological processes, causing excess collagen deposition, leading to inefficient gas exchange leading to death. Current development looks at gene and drug delivery to the distal lung, with a focus on gene therapy for the treatment of IPF, using hepatocyte growth factor (HGF) for alveolar cell repair and regeneration to reduce fibrosis [1].

A major challenge in gene therapy is the delivery of the substances into living cells avoiding side effects. The cell membrane offers a powerful barrier to protect the interior of the cells from any intruders. For gene therapy this membrane has to be conquered effectively. There are different procedures for gene transfer, based on viral vectors and nonviral methods. Transduction uses viruses, which host the gene and introduce it as a part of their replication cycle. However, prominent local and systemic inflammatory and immunogenic response, leading to viral vector toxicity, restricts the clinical application of this system. In contrast non-viral methods such as the use of short and intense electrical pulses (ranging from microseconds to milliseconds; kilovolts per centimeter) applied to cells or tissues, 'electroporation', offers a different mechanism for substances to enter the interior of cells. As a response to an electrical field, the cell membrane temporarily loses its semipermeable properties, leading to ion exchange, the escape of metabolites and an increased uptake of drugs, molecular probes, and genes. The feasibility of electroporation for sustained gene expression in vivo has been show previously in various organs including the lung.

Nevertheless the use of electroporation in therapeutic instruments seems to be limited. To our knowledge, there is currently only one device in development utilizing the electroporation effect to deliver anti-cancer drugs to intraluminal tissue for electro-chemotherapy [2].

Further, nonviral gene transfer of substances into cells (transfection) may be performed by the use of an electrospray process [3, 4], in which likely charged droplets are accelerated towards an oppositely charged electrode by an electrical field. In addition, the likely charged droplets are affected by Coulomb repulsion. Further, a formation of small droplets is caused by "Coulomb explosion" or "Coulomb fission", wherein said Coulomb repulsion is (among others) responsible for the distribution of the formed droplets.

The electrode nearby the targeted tissue guides a droplet bombardment towards the tissue, providing a high impact velocity for the collision with the cell membrane. The feasibility of this process for transfection has already been demonstrated by using water droplets [3], a plasmid suspension incorporating gold nanoparticles [4], as well as a pure plasmid suspension[4]. However, these concepts rely on the requirement of a counter electrode at or below the target plate, thus yielding a set up that is less suitable for clinical practice.

For instance, US 2009/088700 A1 teaches how to use an electrospray within the human body using a tubular device. However, the targeted tissue is grounded via an external electrode connected to the patient and therefore does not provide a single port access toward the region of interest. Furthermore, it does not offer a defined working distance between the human body and the device, and therefore it might be difficult to control the spray process precisely, leading to an unspecified electrospray process and consequently a poorly controlled transfection efficiency.

Therefore, the problem underlying the present invention is to provide for an improved electrospray device, particularly regarding clinical practice.

This problem is solved by a device having the features of claim 1.

According thereto, the claimed device is designed to spray charged droplets of a liquid towards a target along a spraying direction, particularly so as to deliver said liquid or a substance contained therein into a cell or a plurality of cells forming said target, wherein particularly the cell membrane of the respective cell is overcome due to the impact energy of said droplets (which may optionally enhanced by using electroporation), such that the liquid/substance can be delivered into the respective cell without destroying the latter. The device according to the invention further comprises a reservoir (e.g. some volume) for receiving/delivering the liquid to be sprayed, a first electrode being arranged at an outlet of said reservoir for electrifying a meniscus of said liquid at said outlet, at least one second electrode forming a counter electrode to the first electrode for accelerating said droplets due to an electric field between said first and second electrode, and a housing holding the reservoir as well as said electrodes. When being in contact with the tissue, the tissue itself forms part of the second electrode, i.e. a counter electrode.

According to a further embodiment of the invention, an end region of the second electrode, which may form a contact area (interface) for the targeted tissue, is spaced apart from said outlet (or from said first electrode) along the spraying direction. Thus, a pre-defined acceleration stage can be provided for a controlled acceleration of the droplet to be electrosprayed.

According to a further embodiment of the invention, said housing comprises a spray chamber (cavity) extending along the spraying direction, wherein the reservoir is connected to the spray chamber via said outlet that opens into/towards the spray chamber, and wherein the spray chamber comprises an opening facing said outlet along the spraying direction for ejecting the droplets out of the spray chamber. Thus, arranging said opening at or close to the target (tissue) yields a pre-defined working distance of the device allowing for a reproducible electrospray process.

According to a further embodiment of the invention, the first electrode comprises a tubular shape and may be formed (at least in sections) as a hollow circular cylinder, wherein particularly the first electrode is designed to encompass the liquid in the reservoir or to delimit the outlet of the reservoir. Particularly, the first electrode is made of a conducting material and forms said reservoir or at least a section thereof or may be formed as a conducting coating (or element) of the reservoir.

According to a further embodiment of the invention, the first electrode may be coated or covered with an electrically isolating material.

Particularly, said outlet may form a nozzle for supporting spraying of said droplets. Further, the reservoir may comprise a plurality of outlets, each being preferably delimited (surrounded) by a region of the first electrode.

According to yet another embodiment of the invention, the first electrode projects into the spray chamber. Particularly, the first electrode may comprise a region or section arranged on an inside of the spray chamber, which inside extends along the spraying direction, wherein particularly said region may circulate along said inside across the spraying direction.

According to a further embodiment of the invention, the second electrode is arranged at least in sections on a face side of the housing delimiting said opening.

Particularly, in this regard, the second electrode forms a contact area being designed to contact said target onto which said liquid is to be sprayed, so that the target (tissue) has the same potential as the second electrode, and thus actually forms (a part) of the second electrode.

Further, said contact area may have a microstructure allowing for an improved removal of liquid gathering between the contact area and the target. Herewith, an accumulation of liquid on the bottom (target) that may be caused by a continuous delivery of liquid to the target can be reduced. Such an unwanted accumulation of liquid is likely to result in a change of the electrical field, which increases the risk of an electrical discharge. Furthermore droplets have to overcome this fluidic barrier. This will lead to a reduced impact velocity and a lower transfection rate. Further, to overcome this issue the amount of fluid to be delivered to the target can be reduced.

In order to prevent the afore-mentioned unwanted accumulation of liquid, the spray chamber may comprise a plurality of lateral through-holes according to a further embodiment of the invention. Liquid that accumulates inside the spray chamber can then be discharged through said lateral holes In an alternative embodiment, the second electrode may comprise a circumferential free end region protruding from or out of the spray chamber towards the target (e.g. human tissue), wherein preferably said free end region comprises or consists of an electrically conducting wire mesh.

In yet another embodiment of the present invention, said circumferential free end portion of the second electrode may be formed out of an electrically conducting material permeable to the sprayed liquid, e.g. some porous material.

According to a further embodiment of the present invention, the second electrode is arranged completely within the spray chamber, particularly on a boundary region of an inside of the spray chamber, which boundary region delimits the opening of the spray chamber.

According to a further embodiment of the invention, the second electrode is arranged along the opening of the spray chamber, wherein the second electrode particularly circulates along the opening of the spray chamber, i.e., is arranged circumferentially along the opening of the spray chamber.

According to a further embodiment of the present invention, the second electrode, particularly a free end portion protruding from the spray chamber (e.g. along the spraying direction or longitudinal axis of the device or spray chamber) is designed to be expandable at the target concerning its diameter so that a target area delimited by the second electrode is enlarged. For instance, the second electrode or said free end portion may consist out of a flexible, particularly elastic or superelastic material (e.g. Nitinol), such that when the device is pushed out of an (e.g. extended) tubular device (see below) the second electrode or said free end portion of the second electrode expands radially so as to increase said diameter of the second electrode/free end portion of the second electrode. Likewise, when pulling the device back into said tubular device, the second electrode or free end portion of the second electrode is contracted radially and the diameter is correspondingly reduced again.

In the above case, the second electrode or free end portion of the second electrode is preferably self-expanding (e.g. due to its elasticity). However, in a further embodiment, the second electrode or the free end portion of the second electrode can be designed to be expanded and/or contracted by means of an actuation means either manually or automatically.

According to a further embodiment of the present invention, a connection (which may e.g. be provided by one, two or several conductors) of the second electrode to a voltage source (see e.g. below) and/or the second electrode itself is (e.g. at least partly) shielded from the first electrode by an electromagnetic shielding. The shielding is preferably made out of or comprises an electrically conductive material, wherein said shielding is preferably electrically connected to an electrical potential ranging from the potential of the first electrode up to a potential below the potential of the second electrode. Preferably, said shielding as well as particularly its geometry allows for influencing/shaping the electrical field generated by the first and second electrode (and the shield), and therefore particularly allows for a control of the electrospray process.

According to an embodiment of the invention an electrically shielded connection of the second electrode to the voltage source in the form of one, two or several coaxial conductors (e.g. coaxial cables) comprising an inner conductor and an outer conductor surrounding the inner conductor, respectively, is provided, wherein the inner and the outer conductor are arranged coaxially with respect to each other, wherein the second electrode is connected to the respective inner conductor, while the respective outer conductor forming said shielding is connected to a different electrical potential ranging between a potential being larger than the potential of the second electrode and the potential of the first electrode. In particular, the shielding may be connected to the same potential as said first electrode.

According to yet another embodiment a cylindrical shielding (i.e. a cylindrical shielding electrode) is provided, which surrounds the first electrode and is particularly coaxially arranged with respect to the first electrode. With respect to the radial direction of the cylindrical shielding, the conductor(s) connecting the second electrode to the voltage source extend(s) adjacent to the cylindrical shielding, but outside the cylindrical shielding.

In order to be able to observe an individual electrospray process, e.g. the formation of the droplets and their acceleration towards the target, the spray chamber particularly comprises at least one window according to a further embodiment of the invention.

Preferably, two such windows are provided, which face each other across the spraying direction.

According to another embodiment of the invention, the second electrode comprises at least two separate electrode elements (or even more), wherein the device is configured to switch these electrode elements so as to form a single counter electrode to the first electrode for accelerating said droplets. Once the droplets are accelerated as intended, the device is designed to generate a potential difference between said electrode elements so as to generate an electroporation of the droplets injected into the target in addition. Preferably, these electrode elements face each other across the spraying direction, e.g. are distributed around the spraying direction.

Preferably, the electrode elements are formed/arranged symmetrically, e.g., in the case of two electrode elements the latter may be formed as half rings. In case of four electrode elements the latter may be formed as quarter rings. Generally, a number of electrode elements may be provided which may be arranged (equidistantly distributed) one after the other along the opening of the spray chamber. The entirety of the electrode elements then forms said contact area, particularly.

For generating the necessary potential difference, the device comprises a (controllable) voltage source that is preferably connected via suitable conductors (e.g. wires) extending from the voltage source to the housing's first and second electrode(s). The housing may provide suitable contacts for these conductors. Particularly, the voltage source is designed to generate a high voltage (potential difference) in the range of 1 kV and 25 kV (other ranges may also prove to be suitable) between the first electrode and the second electrode(s), so as to accelerate said droplets towards said target resulting in transfection. The voltage source may operate in a continuous or in a pulsed mode.

According to an embodiment of the present invention, the device is configured to set the second electrode by means of the voltage source on a potential different from ground as well as different from the first electrode, particularly so as to enhance electroporation of the droplets injected into the target by increasing a membrane potential of said tissue (cells).

According to a further embodiment of the invention, the electrodes described above are integrated into the housing resulting in a very compact device.

According to an embodiment of the invention the housing comprises an inner part and an outer part encompassing said inner part, wherein the first electrode is held by said inner part and wherein the second electrode is held by said outer part. For this, the housing may comprise a first collet means for holding the first electrode or a conductor (for connecting the first electrode to a voltage source) connected to the first electrode, wherein particularly said inner part comprises the first collet means, as well as a second collet means for holding at least one conductor (e.g. two conductors) connected to the second electrode, wherein particularly said outer part comprises the second collet. Via said conductors, the second electrode can be connected to the voltage source.

According to another embodiment of the invention, the housing or at least a free end or face side of the housing delimiting said opening of the spray chamber is made out of a flexible material such as silicone in order to reduce the risk of damaging/injuring the target when using the device.

According to another embodiment of the invention, the housing, the (e.g. integrated) first electrode and the second electrode may be realized from flexible material to obtain a flexible device. In particular, the housing can be made of a flexible polymer (e.g. PDMS) and the electric conductive material used for said electrodes may be a conductive polymer, a flexible metal (e.g. a nickel titanium alloy (NiTi), also known as Nitinol, which is a metal alloy of nickel and titanium, where the two elements are present in roughly equal atomic percentages, particularly 50% to 60% Ni and e.g. 40% to 50% Ti depending on the Ni concentration and eventually other components that may be used in a TiNi alloy. NiTi alloys exhibit shape memory as well as superelasticity (also denoted as pseudoelasticity). Shape memory means the ability of the alloy to undergo deformation at one temperature, while the initial undeformed shape is recovered upon heating above the transformation temperature of the alloy. Superelasticity occurs at a narrow temperature range just above said transformation temperature; in this case, no heating is necessary to cause the undeformed shape to recover, and the material exhibits enormous elasticity (e.g. 10-30 times that of ordinary metal). Here, the NiTi alloy or another alloy is preferably chosen such that elasticity particularly superelasticity occurs in a temperature range that comprises the temperature of the target or a temperature during application of the electrospray device.

Said alloy may be formed in a flexible geometry (e.g. a coil). Further, besides NiTi, also metals (e.g. steel) or other alloys formed in a flexible geometry (e.g. a coil) may also be used.

Further, multiple use of the device may results in a moistening of the housing (body), leading to an increased risk of electrical discharge. Therefore, the housing or parts thereof (particularly the spray chamber) are preferably formed out of or coated with a hydrophobic or super hydrophobic material, or contain nano- or microstructures in order to obtain hydrophobic or super-hydrophobic properties. Superhydrophobic surfaces are highly hydrophobic. In this case the contact angle of a water droplet exceeds 150°. This is also referred to as the Lotus effect.

According to another embodiment of the invention, the device may be formed from two-dimensional (sheet-like) material layers. For instance, the first electrode may be formed by a rolled up conductive layer. Further, the second electrode may be formed by a rolled up conductive layer. Likewise, the housing may comprise a rolled up insulating layer rolled around the first electrode defining the spray chamber and particularly a second insulating layer rolled around the second electrode (which is particularly rolled around said insulating layer defining the spray chamber).

According to yet another embodiment of the invention, the device may comprise a plurality of second electrodes arranged one after another in the spray chamber along the spraying direction, wherein each two neighboring second electrodes form a pair of electrodes, wherein the first pair is formed by the first electrode and the closest second electrode along the spraying direction. Here, the device is configured to generate with help of the voltage source a potential difference between said pairs in a subsequent fashion along the spraying direction starting from the first pair, then between the second pair and so forth, so as to accelerate said droplets between each pair of electrodes along the spraying direction. This configuration can be compared to a peristaltic pump and allows for a formation of the electrospray at a lower voltage. In other words, the device provides for a plurality of acceleration stages for the droplets.

According to a further embodiment of the present invention, the second electrode (or the plurality of second electrodes) is formed to be fluidic transparent. Therefore, the second electrode(s) particularly comprise a plurality of recesses through which said accelerated droplets can pass the second electrode along the spraying direction on their flight towards the target. For instance, such a second electrode may be formed as a grate or comprises at least one clamp, particularly a plurality of (e.g. parallel) clamps. This allows the second electrode to extend parallel to or in front of the opening of the housing (e.g. in the spray chamber) without actually blocking the opening for the droplets.

According to a further embodiment of the invention, the device comprises a means for generating a gas flow along the spraying direction around the reservoir or first electrode, particularly so as to confine the droplets (spray) and/or reduce the risk of corona discharge and/or to generate a defined gaseous environment within the spray chamber. Further, some gases (like carbon dioxide) have a higher dielectric strength. Furthermore, the flow of a dry gas removes humidity and thus helps to prevent a discharge.

In this regard, the device may comprise a slit extending around the reservoir (inner part of the housing) through which said gas may flow into (and through) the spray chamber for providing said environment.

According to yet another embodiment of the invention, the housing (body) of the device comprising the reservoir, spray chamber and electrodes is designed to be inserted into a working channel of an (e.g. extended) tubular device (at a distal end of the latter), wherein said tubular device is particularly formed as an endoscope, particularly a bronchoscope. This allows one to position the housing close to the respective target (e.g. distal lung).

According to a further object of the invention, a system is proposed, comprising an (e.g. extended) tubular device, particularly in the form of an endoscope or a bronchoscope, and a device according to the invention, wherein the housing is inserted into a working channel of the tubular device (at its distal end) for arranging said housing at the target.

According to a further object of the invention, a method for producing a device according to the invention is proposes, the method comprising the steps of:
  rolling up a first conductive layer so as to form an (e.g. cylindrical) first electrode,
  rolling a first insulating layer around the first electrode forming a first part of a housing of the electrospray device, which first part delimits a spray chamber of the electrospray device,
  rolling a second conductive layer around said rolled first insulating layer so as to form a second electrode, and
  particularly rolling a second insulating layer around the second electrode so as to form a second part of the housing.

According to a further object of the invention, a method for delivering a substance into a cell or a plurality of cells forming a target is proposed, the method comprising the steps of: Accelerating charged droplets of a liquid comprising said substance out of a reservoir (storage volume) towards said target by means of an electric field generated by means of at least a first and a second electrode such that said droplets or said substance contained in the droplets overcome the respective cell membrane, particularly without destroying the respective cell, wherein said reservoir and said electrodes are arranged in or integrated into a housing that is particularly delivered to said target via a (working) channel of an (e.g. extended) tubular device, particularly an endoscope, particularly a bronchoscope, before accelerating said droplets towards the target. Particularly, the second electrode is positioned such that it contacts the target (tissue), so that the latter forms part of the second electrode (counter electrode). Particularly, said cells are distal cells of a lung (in vivo or ex vivo), particularly alveolar epithelial cells. Particularly, said substance is a plasmid, wherein said plasmid can be a reporter plasmid to be used for instance in animals (e.g. as a proof of concept), and wherein preferably the plasmid may contain Human Hepatocyte growth factor (HGF), e.g. for clinical applications to treat Pulmonary fibrosis (see above).

Further, the above described device/method may also be used/conducted with help of an additional external ground electrode positioned below the target. Furthermore, one may merely use such an external ground electrode (instead of the second electrode).

Further, the above described device/method may also be used/conducted with help of an additional external ground electrode positioned below the target. Furthermore, one may merely use such an external ground electrode (instead of the second electrode).

Furthermore, each of the following aspects of the present invention, which are also described above, may be formulated as a sub claim to the independent claim as follows:

According to an aspect of the invention said electrodes (100, 200) are integrated into the housing (30).

According to an aspect of the invention the housing (30) comprises an inner part (30*a*) and an outer part (30*b*) encompassing said inner part (30*a*), wherein the first electrode (100) is held by said inner part (30*a*) and wherein the second electrode (200) is held by said outer part (30*b*).

According to an aspect of the invention the housing (30) comprises a first collet means for holding the first electrode (100) or for holding a conductor connected to the first electrode (100), wherein particularly said inner part (30*a*) comprises the first collet means, and wherein the housing (30) comprises a second collet means for holding at least one conductor (210) connected to the second electrode (200), wherein particularly said outer part (30*b*) comprises the second collet means.

According to an aspect of the invention the housing (30) is made out of a flexible material, particularly silicone.

According to an aspect of the invention the first electrode is formed by a rolled up conductive layer.

According to an aspect of the invention the second electrode is formed by a rolled up conductive layer.

According to an aspect of the invention the housing comprises a rolled up insulating layer rolled around the first electrode defining the spray chamber and particularly a second insulating layer rolled around the second electrode.

According to an aspect of the invention the second electrode (200) defines a plurality of recesses through which said accelerated droplets (D) can pass the second electrode (200) along the spraying direction (S), wherein particularly the second electrode (200) is formed as a grate or comprises at least one clamp, particularly a plurality of clamps.

According to an aspect of the invention the device (1) comprises a means for generating a gas flow along the spraying direction (S) around the reservoir (10), particularly so as to confine the droplets (D) and/or reduce the risk of corona discharge and/or to generate a defined gaseous environment within the spray chamber (31).

According to an aspect of the invention the housing (30) of the device (1) is designed to be inserted into a working channel (501) of an extended tubular device (500), particularly in the form of an endoscope, particularly in the form of a bronchoscope, for arranging said housing (30) at the target (T).

Further, according to an aspect of the present invention a further independent claim may be directed towards a Method for producing a device for spraying charged droplets of a liquid towards a target along a spraying direction, comprising the steps of:

- rolling up a first conductive layer so as to form a first electrode (100),
- rolling a first insulating layer around the first electrode (100) forming a first part of a housing (30) of the device (1), which first part delimits a spray chamber (31) of the device (1), rolling a second conductive layer around said rolled first insulating layer so as to form a second electrode (200), and particularly rolling a second insulating layer around the second electrode (200) so as to form a second part of the housing.

Further features and advantages of the invention shall be described by means of detailed descriptions of embodiments with reference to the Figures, wherein FIG. 1 shows a concrete example of a device according to the invention;

Figure 16:
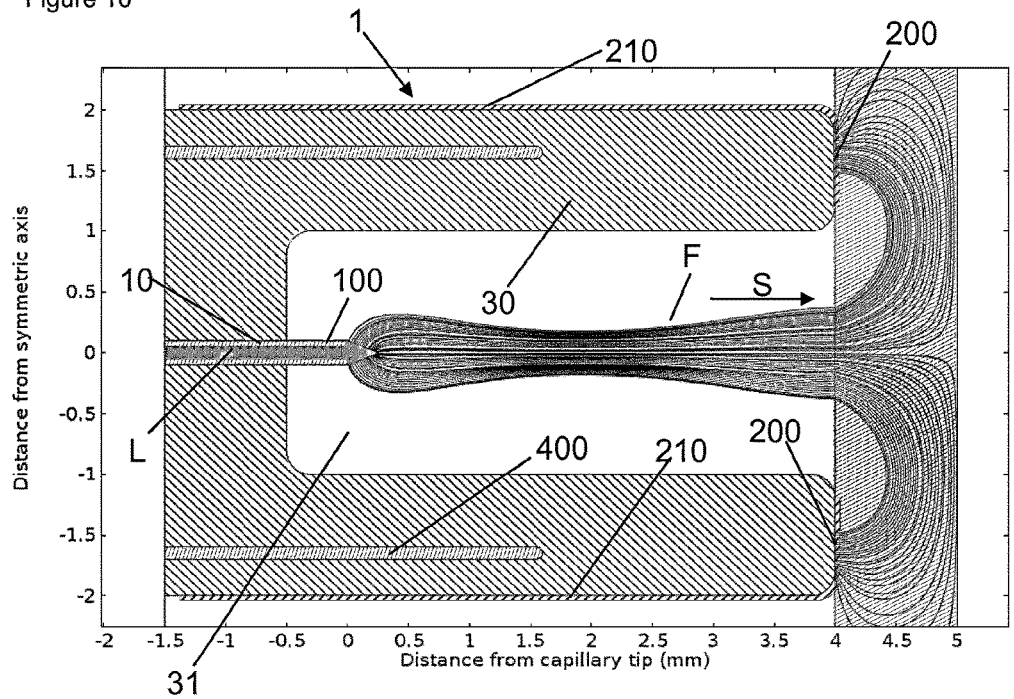
Figure 17:
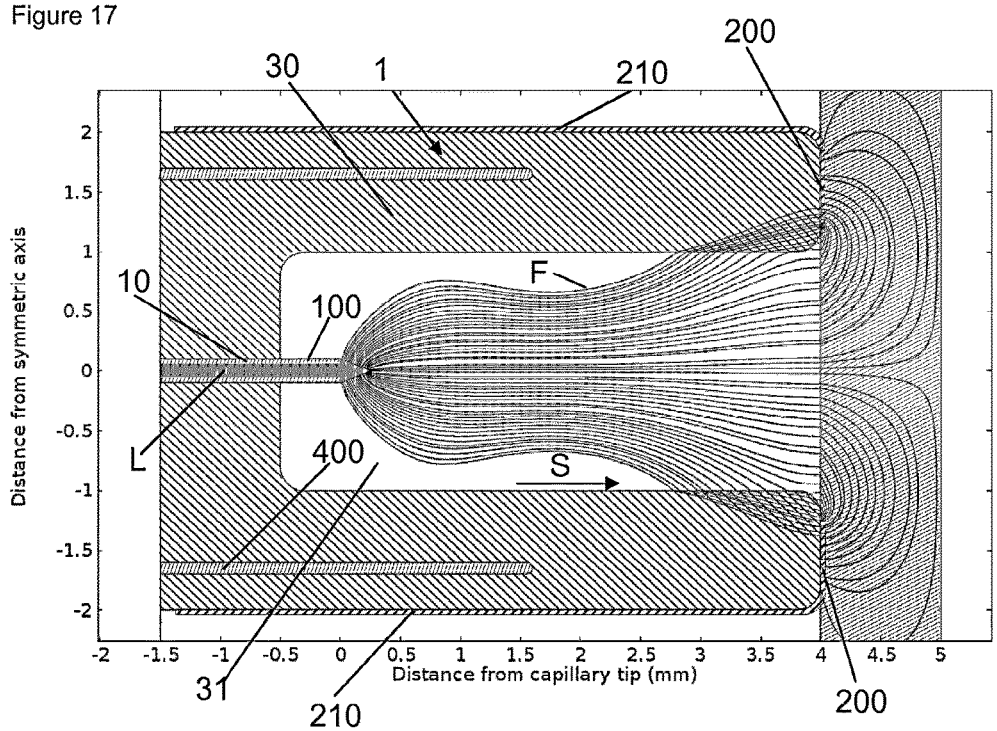
Figure 18:
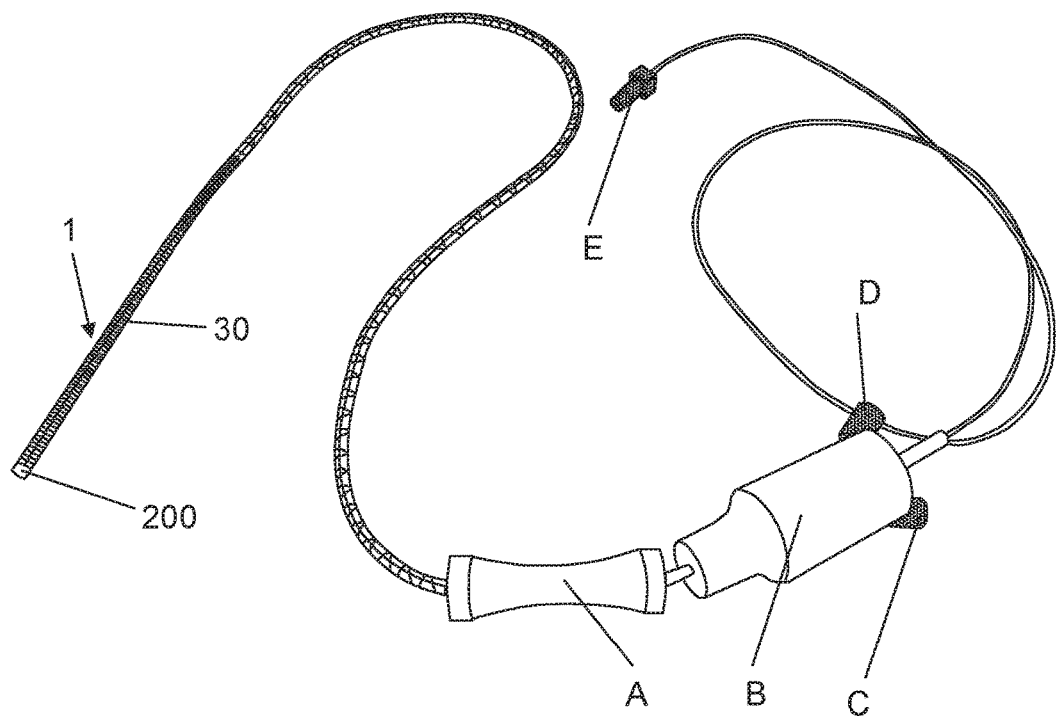
Figure 19:
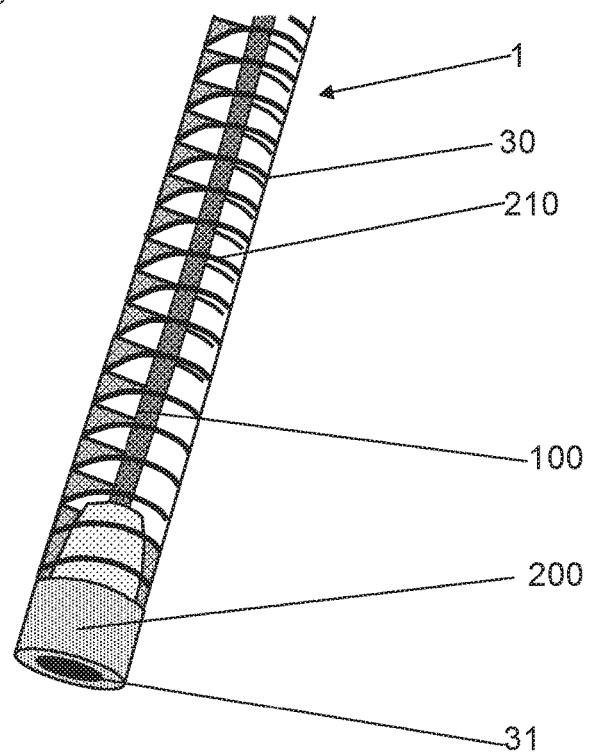
Figure 20:
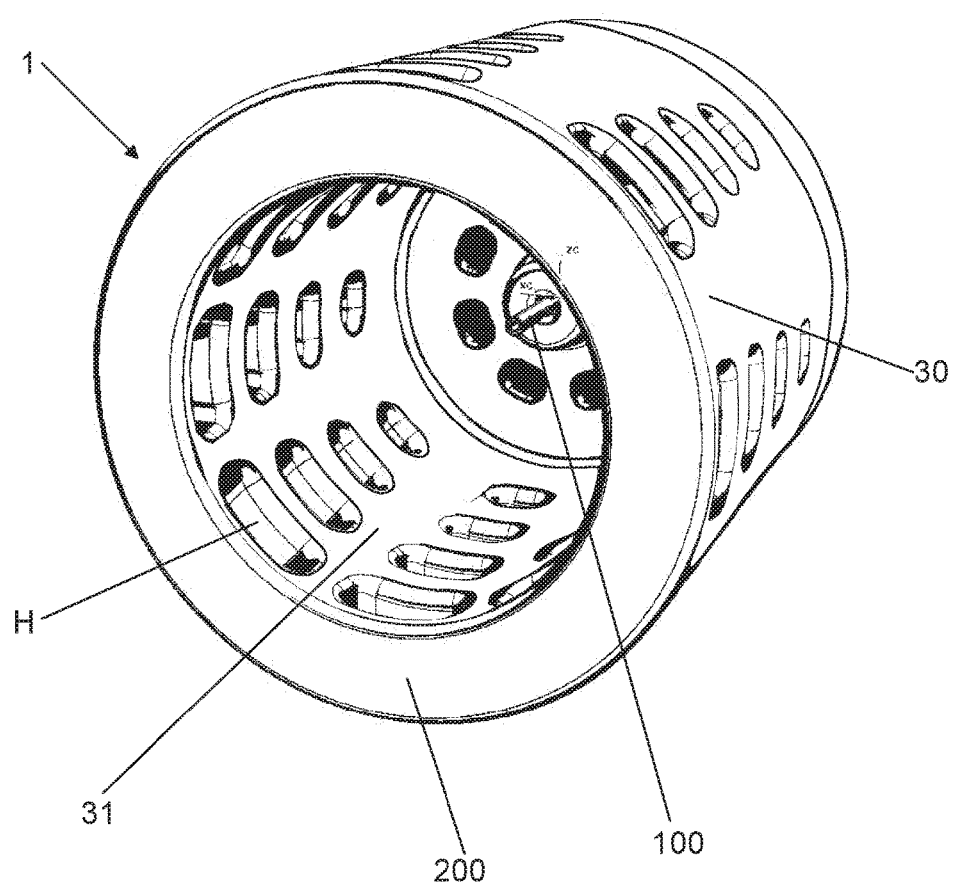

FIG. 16 shows a further example of a device according to the invention (diameter 4 mm, working distance 4 mm), wherein a conductive shielding is provided within the housing of the device, extending 1.6 mm axially into the spray chamber (which is 40% of the working distance) and connected to the same potential as the first electrode (3.5 kV);

FIG. 17 shows the exemplary device shown in FIG. 16, wherein the shielding is connected to a potential in between the potentials of the first and the second electrode, 2.5 kV in particular;

FIG. 18 shows an example of a flexible electrospray device according to the invention, consisting of a PDMS tubing with a flexible NiTi (e.g. Nitinol) tubing providing the fluid delivery (e.g. reservoir) and as the first electrode, and a coil shaped conductor for connecting the second electrode to the voltage source;

FIG. 19 shows a close up of the tip of the reservoir of the device shown in FIG. 18; and FIG. 20 shows a device according to the invention having through-holes in the housing connecting the spray chamber to a surrounding so that liquid that has accumulated inside the spray chamber can be discharged out of the spray chamber.

FIGS. 1 to 5 show devices 1 for a nonviral gene transfer to e.g. the lung tissue by the use of an electrospray process. Droplets D containing a negatively charged liquid L (e.g. a plasmid) are accelerated towards a positively charged second electrode 200 by an electrical field along a spraying direction S. In addition, the likely charged droplets D are affected by Coulomb repulsion and explosion, and experience an additionally accelerating force. This interaction leads to the formation of very small sized droplets D. It is to be noted, that the polarity of the electrodes 100, 200 as shown in the FIGS. 2 to 5 depends on the specific liquid L and corresponds to the one used with plasmid L. Of course, the polarity shown in FIGS. 2 to 5 may also be reversed (for instance, in case of other liquids L, the second electrode 200 may actually be negative while the first one 100 may be positive).

In case of plasmid L the positive second electrode 200 nearby the targeted tissue (target) T guides a droplet D bombardment towards the tissue T, providing a high impact velocity for the collision with the cell membrane of the tissue T.

Figure 2:
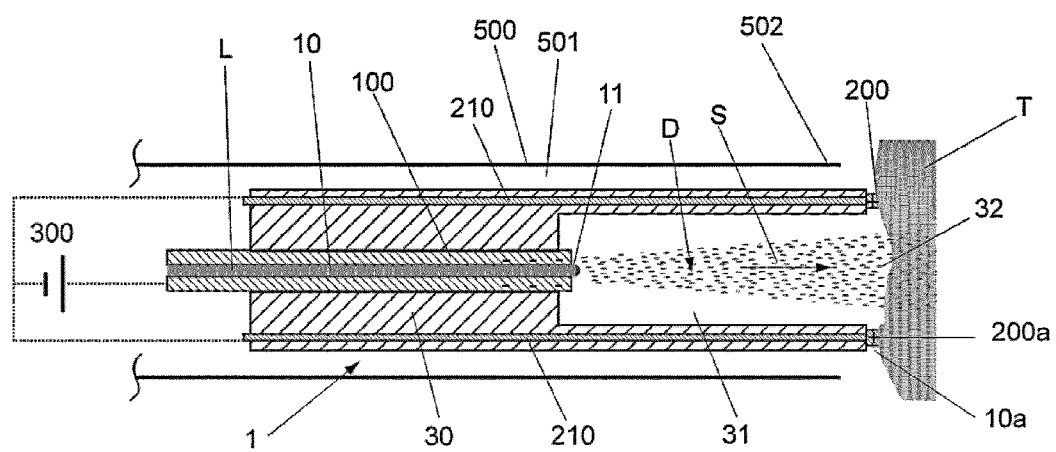
FIG. 2 shows a schematical view of a device of the kind shown in FIG. 1.
Figure 11:
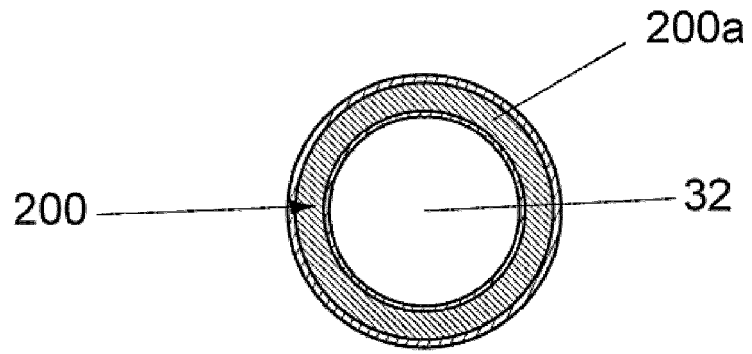
FIG. 11-14 show possible shapes of second electrodes (contact areas)

According to FIG. 2 showing a schematical illustration of an electrospraying device 1 according to the invention, the device 1 comprises a housing 30 for receiving the components of the device 1, particularly a reservoir 10 for providing/delivering the liquid L that is to be sprayed into the target T along a spraying direction S (here, the reservoir 10 is a conduit being in fluid connection to a syringe pump), as well as a first electrode 100 and a second electrode 200 forming a contact area 200a for contacting the tissue T, which contact area 200a is spaced apart along said spraying direction S (working distance) from an outlet 11 of the reservoir 10, which is actually delimited/formed by the tubular first electrode 100. The housing 30 further delimits a spray chamber 31 extending along the spraying direction S from the outlet 11 to an opening 32 of the spraying chamber 31 along which opening 32 the second electrode 200 circulates with its contact area 200a in an annular manner as shown in FIG. 11. Generally, the second electrode 200 may be contacted by means of two conductors 210 extending along the housing 30. Said conductors 210 may also be replaced by a region (conductor) 210 of the second electrode 200 being formed as a cylinder encompassing the first electrode 100. In case of two conductors 210, the latter are preferably symmetrically arranged with respect to a longitudinal axis of the housing 30 extending along the spraying direction S.

The second electrode 200 serves as a ground electrode, which is used to ensure the ground potential at the tissue T. Preferably, the second electrode 200 is integrated into the housing 30. A high voltage to generate the electrical field is connected to the first electrode 100, which also delivers the liquid L (see above). Due to the spray chamber 31 within the housing (also denoted as body) 30 a predefined working distance is provided between the electrodes 100, 200, and therefore, assuming constant electrical conditions within the spray chamber 31, a defined electrical field for the electrospray process. Furthermore, the spray chamber (cavity) 31 reduces the effect of changes in the surroundings, e.g. alternating airflow due to respiration.

Now, electrospraying of the droplets D is based on the migration of droplets D emitted from an electrified meniscus at the outlet 11 of the reservoir 10/first electrode 100 towards the second (counter) electrode 200. In this process, electrically charged droplets D are accelerated due to the interaction with the electrical field generated by the electrodes 100, 200 and affected by the Coulomb repulsion between the droplets D. Additionally, these forces will disrupt the droplets D even more. Therefore very small droplets D, travelling at high velocities are obtained that can pass the individual cell membrane. In contrast to other aerosol generating systems, e.g. ultrasonic or pressure driven nebulizers, no mechanical movement of components or airflow is required.

Figure 1:
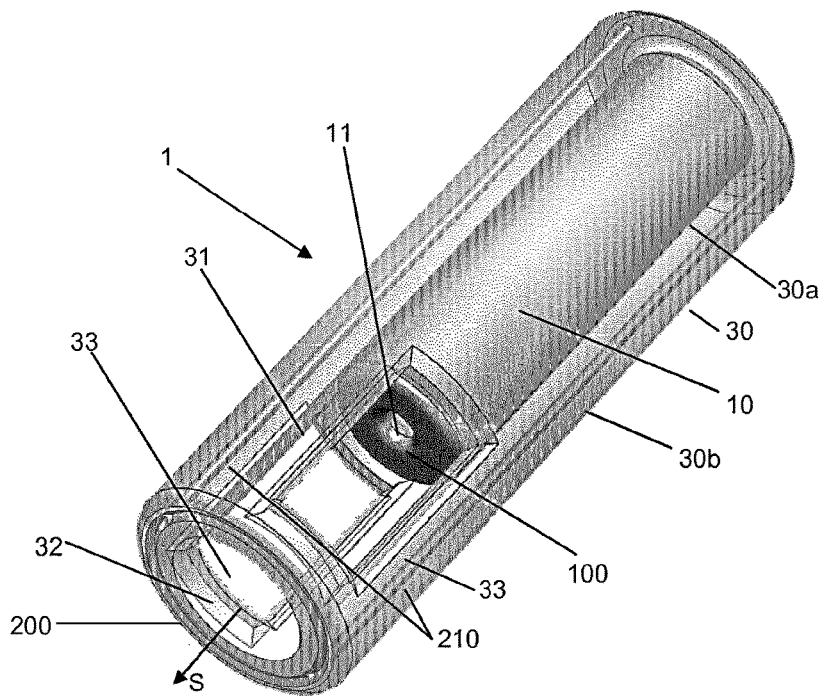

FIG. 1 shows an example of a device according to FIG. 2. Here, the housing (body) 30 was manufactured using an additive manufacturing processes using an Eden250™ 3D Printing System (Objet) to process a photopolymer (Full-Cure®850 VeroGray from Objet).

For improved experimental flexibility the housing 30 (FIG. 2) consists of two pieces, namely an inner part 30a, containing a first collet means for the first electrode in the form of an conductive pipe 100 forming also the reservoir 10, and an outer part 30b, containing a second collet means for an electrical connection (conductors 210) to the second (ground) electrode 200. To assure a symmetrical electrical field the two conductors 210 provided for the ground electrode 200 are symmetrically arranged (e.g. parallel to the spraying direction S on opposite sides of the housing 30). However, this is only one example. Instead of the two conductors 210 also a single conductor (e.g. a foil wrapped around housing 30) or even more than two conductors 210 may be used.

Furthermore, the housing 30 comprises two windows 33 in the region of the spray chamber 31 to be able to observe the electrospray process visually. The outer dimensions of the body are 30 mm length by 10 mm diameter. However, these dimensions can be tailored with respect to the actual application and are thus not fixed. Instead of such windows 33 or in addition, the spray chamber 31 may comprise a plurality of through-holes H according to FIG. 20 through which liquid L that has accumulated in the spray chamber can be drained out of the spray chamber 31.

For the ground electrode connection (conductors 210) preferably stainless steel (1.4310, Ø300 µm) is used. The ring shaped contact area (interface) 200a of the second electrode 200 and the tissue is realized using a conductive paint (Graphit 33, CRC Industries).

Figure 6:
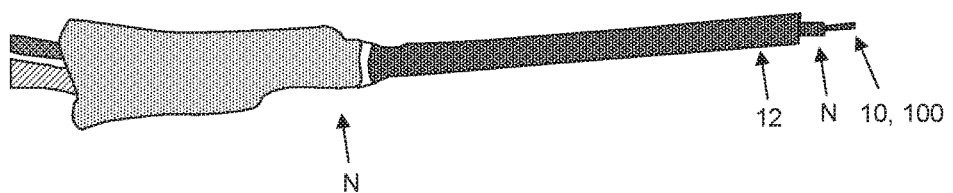
FIG. 6 shows an exemplary set up of an electropolished conductive pipe, a standard needle, and an additional isolation (inner part of device according to FIG. 1)

Further, FIG. 6 shows an exemplary setup of the pipe arrangement (inner part 30a), wherein the conductive pipe 100 consists of a stainless steel tubing (SUS316L, 28G tubing, o.Ø 360 µm, i.Ø 170 µm, ~50 mm length) inserted for stability purposes within a standard 21G needle N. The edges of the pipe 100 are deburred by an electropolishing procedure. The pipe 100 is connected to the fluid reservoir 10 (FEP tubing) and offers a high voltage electrical connection. Additionally, the complete arrangement is insulated using heat shrink tubing 12.

The complete assembly according to FIGS. 1, 2 and 6 creates a working distance from the exit port (outlet 11) of the pipe (first electrode) 100 to the second (counter) electrode 200 of 8 mm.

For the delivery of the liquid L to the reservoir 10, a precision syringe pump (cetoni neMESYS, with 500 µl glass syringe) is connected to the pipe 100, enabling delivery of a predefined volume at a predefined flow rate. A high voltage source (FuG HCP 35-6500 MOD, AIP Wild AG) 300 (c.f. also FIG. 2) was connected to the device 1 to generate the electrical field. It can be used in pulsed or continuous mode.

Figure 3:
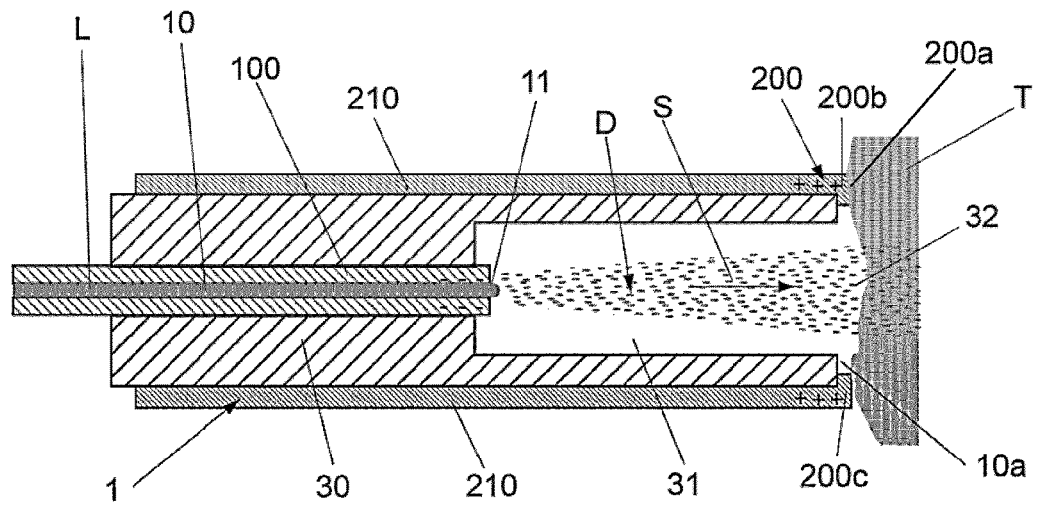
FIGS. 3-5 show further schematical views of variants of devices according to the invention.
Figure 4:
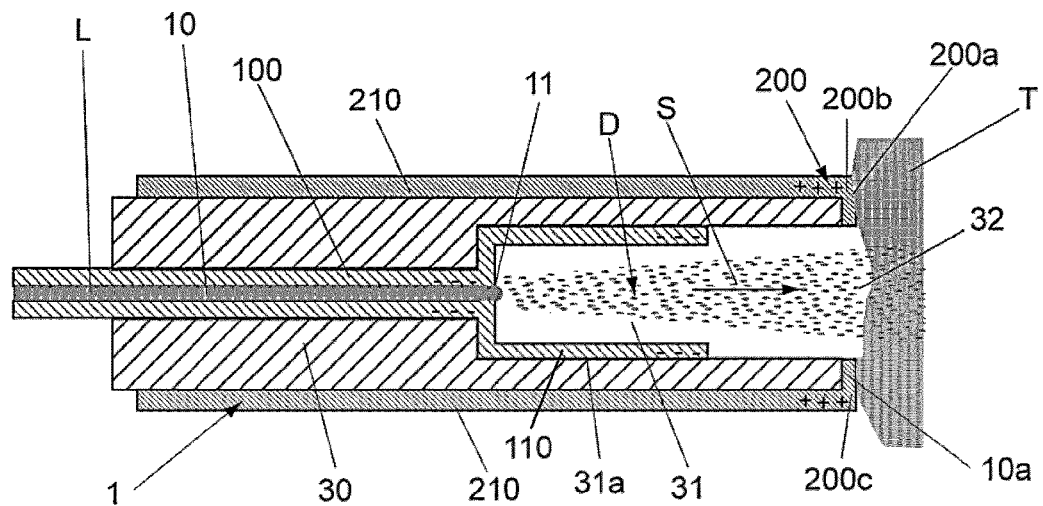
Figure 5:
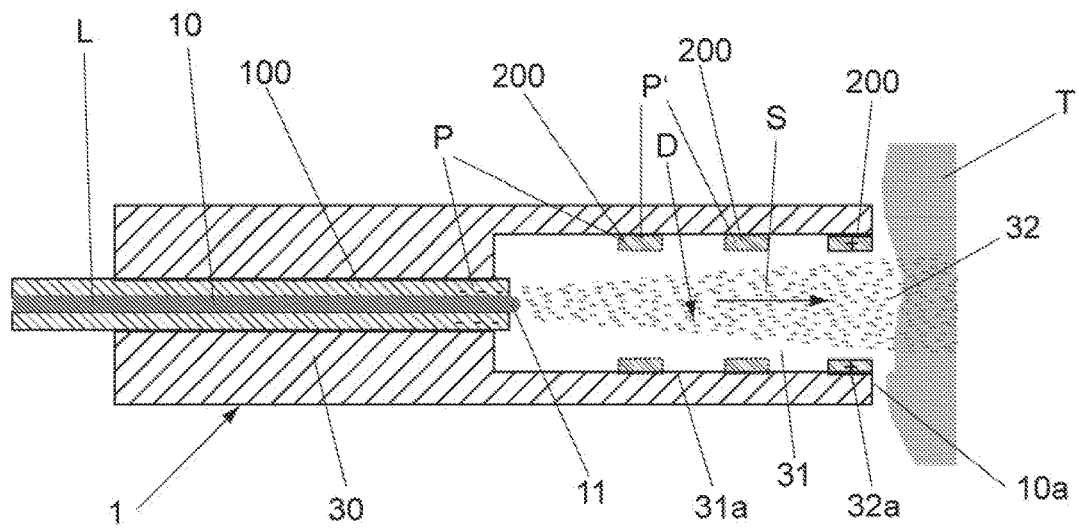
Figure 12:
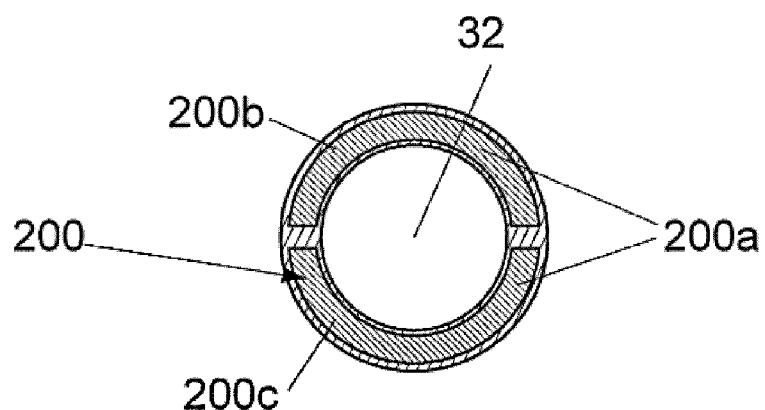

FIGS. 3 to 5 show modifications of the device 1 according to FIG. 1 (see FIG. 2 concerning connections to a voltage source 300). According to FIG. 3 the second electrode 200 may extend along an outside of the housing 30 along the spraying direction S with a cylindrical region 210 or separate conductors 210 and reaches behind a face side 10a of the housing 30 delimiting the opening 32 of the spray chamber 31 so as to form a contact area (interface) 200a for contacting the respective target T. Said contact area 200a may circulate along the opening 32, i.e., may be shaped as a ring. The second electrode 200 may have a cylindrical shape encompassing the housing 30 at least at the opening 32 of the spray chamber 31 or may be separated into two electrode elements 200b, 200c at said opening 32 facing each other across the spraying direction S as shown in FIG. 12. Such separate electrode elements 200b, 200c can be shaped as half rings according to FIG. 12 and may also be contacted by conductors 210 in the form of wires as described with respect to FIGS. 1 and 2.

In case of two electrode elements 200b, 200c, the latter may be switched by the device 1 to form a single second (counter) electrode 200 for accelerating the droplets D. Thereafter, a potential difference is applied to the electrode elements 200b, 200c by the device 1 so as to generate electroporation for enhancing delivery of the droplets D or the substance contained therein into the respective cells (target T).

Figure 13:
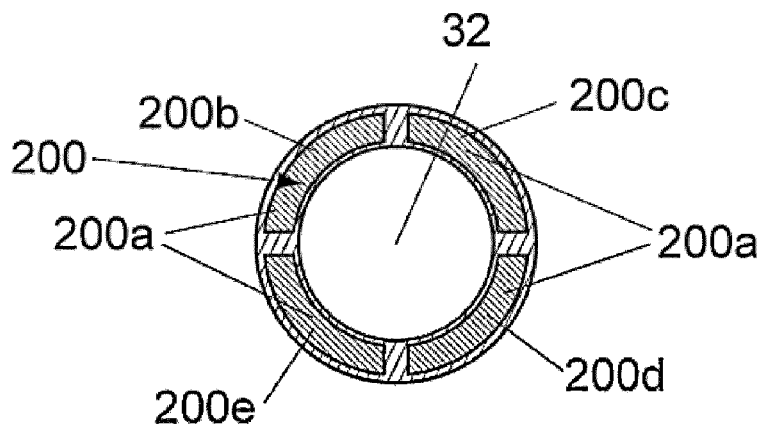
Figure 14:
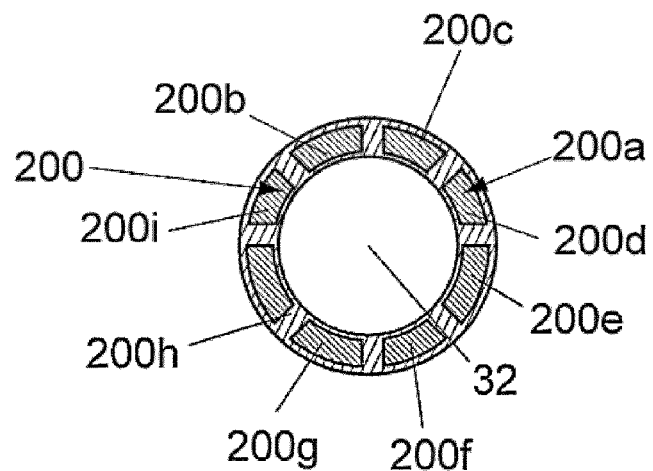
Figure 15:
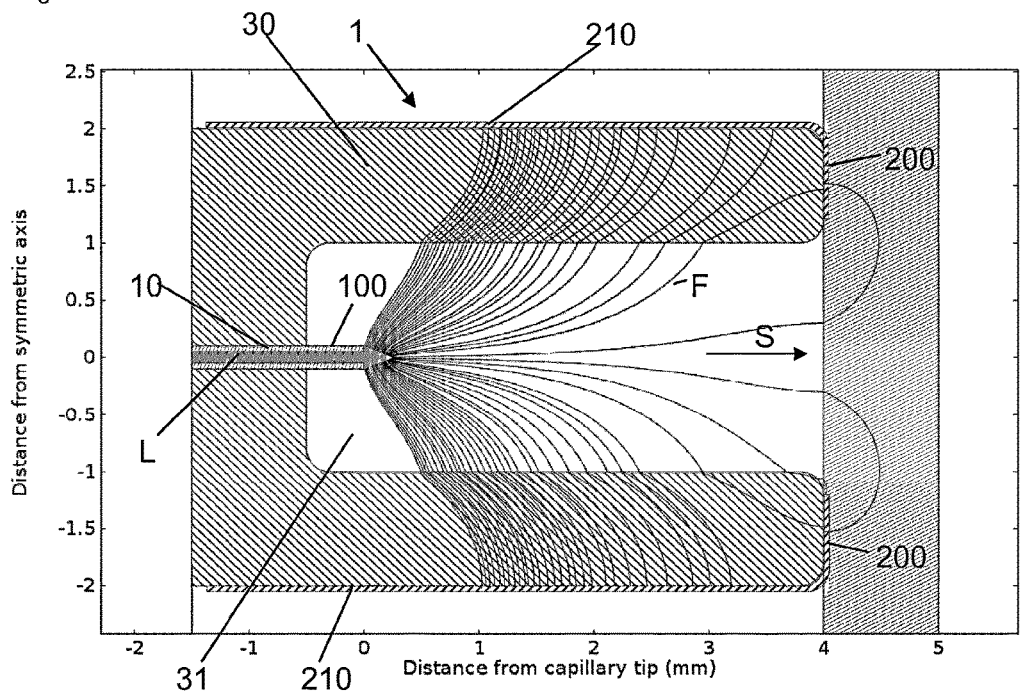
FIG. 15 shows an example of a device according to the invention (diameter 4 mm, working distance 4 mm) and the simulated emerging electrical field, assuming an applied voltage of 3.5 kV at the first electrode and ground at the second electrode.

As shown in FIGS. 13 and 14, also more than two electrode elements 200b, 200c can be provided. In case of FIG. 13, the second electrode 200 comprises four electrode elements 200b-200d distributed along the periphery of opening 32, while there are eight such electrode elements 200b-200i in FIG. 14. The multiple electrode elements 200b-200d, 200b-200i also function as a single second electrode 200 for accelerating the droplets D, while a potential difference may be applied afterwards between these electrode elements in order to generate electroporation.

According to FIG. 4, the first electrode 100 may extend with a region 110 into the spray chamber 31 such that a part of an inside 31a of the spray chamber 31 adjacent to the outlet 11 of the first electrode (pipe) 100 is covered by said region 110.

Furthermore, according to FIG. 5, the second electrode 200 may be arranged completely inside the spray chamber 31. Here, no contact is made between the second electrode 200 and the tissue (target) T. As before, the second electrode 200 being arranged along the opening 32 of the spray chamber 31 may circulate along the opening 32 on a boundary region 32a of the inside 31a of the spray chamber 31 in an annular manner, which boundary region 32a delimits the opening 32 of the spray chamber 31.

Further, the configuration according to FIG. 5 can be used for providing several acceleration stages for the droplets D when an (optional) plurality of second electrodes 200 (see dashed lines) is provided in the spray chamber 31 one after the other along the spraying direction S. Then, these second electrodes 200 (together with the first electrode 100) can be switched in a pairwise fashion (one pair P after the other along the spraying direction S). For instance, initially, the first pair P formed by the pipe 100 and the adjacent second electrode 200 comprises a potential difference that accelerates droplets D towards the opening 32/target T. Then the next pair P' is switched providing again a potential difference accelerating the droplets D that have been accelerated by the first pair P before and so on.

Further, transferring the electrospray process/device 1 according to FIGS. 1 to 6 into a successful therapeutic device may be achieved by the integration of the device 1 within standard diagnostic or interventional procedures. For pulmonary examination this is a bronchoscope for instance. Depending on the application, other tubular devices (endoscopes) may also be used for transporting the device 1 or rather its housing 30 to the target T.

As shown in FIG. 2 as an example, a device 1 according to the invention is preferably placed in a working channel 501 of such an (e.g. extended) tubular device (e.g. bronchoscope) 500 and is displaced therein towards a distal end 502 of said tubular device 500, which distal end 501 is positioned at the location of the target T (e.g. the distal lung for instance). Conductors for contacting the electrodes 100, 200 of the device 1 according to the invention then extend from a voltage source 300 through said working channel 501 towards the housing 30 of the device 1 arranged within the working channel 501 at the distal end 502 of the tubular device 500.

Using a working channel 501 of a tubular device (endoscope) 500 provides a concept using only a single port to access the targeted region T, which is possible since the device 1/housing 30 according to the invention incorporates all relevant functional elements (see also above), i.e., at least a first and a second electrode 100, 200 for generating the electrical field, an acceleration stage where this field is applied and interacts with the liquid L, and a liquid delivery mechanism, to provide the therapeutic dissolved substance or suspension. The electrical field for acceleration is created by said electrodes 100, 200, one formed by the outlet 11 of the electrically conductive pipe 100, containing the liquid L to be delivered, and a counter electrode 200 in contact to the tissue T, for example, thus using the targeted tissue T itself as a counter electrode.

FIGS. 16 to 17 show the calculated influence of an additional symmetric (i.e. cylindrical shielding 400 on the electrical field distribution F shown in solid lines. Charged droplets within the spray chamber 31 will be affected by the electrical field and will attain an accelerating force according the direction of the electrical field lines. Therefore, the field lines F may be roughly interpreted also as flight tracks of the charged droplets. In particular, FIG. 15 shows the distribution F without any shielding, while the devices 1 as shown in FIGS. 16 and 17 comprise a shielding 400. The shielding 400 is formed as a symmetric, particularly cylindrical conductor that surrounds the first electrode 100, wherein said shielding 400 is particularly arranged coaxially with respect to the first electrode 100 that surrounds the reservoir 10 of the respective device 1 as described with respect to FIGS. 1 to 5. The shielding further extends adjacent to the second electrode 200, 210 or close to conductors 210 connecting the second electrode 200 to the voltage source 300, see also above. In FIGS. 16 and 17, the shielding 400 extends 1.6 mm axially into the spray chamber 31, corresponding to 40% of the working distance, i.e., the distance from the tip/end of the first electrode 100 to the target T (e.g. when the device 1 rests against the target T). The electrical field lines F are focused in the radial direction towards the center of the spray chamber 31 of the device 1, depending on the potential applied to the shielding 400. In FIG. 16 the shielding 400 assumes the same potential as the first electrode 100 (3.5 kV), while in FIG. 17 the shielding assumes an electrical potential in between the potential applied to the first and the second electrode 100, 200 (2.5 kV). The cylindrical shielding 400 described with respect to FIGS. 16 to 17 may also be present in the devices 1 shown in FIGS. 1 to 5.

FIG. 18 shows an embodiment of a flexible electrospray device 1 according to the invention having a diameter of 3 mm. The housing 30 is made of Polydimethylsiloxane (PDMS), and includes a flexible tubing, acting as first electrode 100 and providing the liquid L to the spray chamber 31 made of super-elastic Nickel titanium (Nitinol), as well as a coil shaped connection 210 to the second electrode 200. The interface of the second electrode (cup electrode) 200 to the target T is made of brass. Preferably, said liquid L can be delivered through a connection to a syringe pump E. The device 1 further comprises a sheath slide A and a fittings holder B being the main port where the electrodes 100, 200 and the liquid source enter the device, particularly comprising connections to a high voltage D (first electrode 100) as well as to a ground electrode C being the second electrode 200, and wherein sheath slide A provides a book mark which can tell the user the approximate depth of the device 1 inside the body into which the device is inserted.

FIG. 19 shows a close up of the tip of the flexible electrospray device 1 shown in FIG. 18.

EXAMPLES

A. Experimental Set Up and Procedure

We installed the device 1 according to FIGS. 1, 2 and 6 within a stand and placed the target (cell culture and lung tissue) T on standard well plates. The well plate was placed on a height adjustable platform. The height of the well plate was adjusted visually until the device 1 was in contact with the target (cells or tissue slice) T. The voltage was then applied, followed by the syringe pump. To ensure complete fluid (liquid) L delivery there was a delay of 30 seconds before switching the power source off.

B. Cell Culture

A549 cells (alveolar epithelial like cells) were grown to confluence in RPMI growth medium with 10% fetal bovine serum (FBS) in 24-well plates (15.6 mm in diameter). Before electrospray the growth medium was removed and electrospray was performed either in absence of medium or in presence of 100 μl of medium. For electrospraying 50 μg/ml enhanced green fluorescent protein (eGFP) reporter gene suspended in distilled water was used.

The current flow during the spray process was limited to 200 μA, while the applied voltage was set from 5.0 to 6.5 kV. Assuming a homogenous field distribution, this corresponds roughly to an electrical field in the range 0.56 to 0.81 kV/mm. At a flow rate of 100 μl/min we delivered 50 μL of plasmid suspension, corresponding to 2.5 μg of the plasmid. The cell cultures were subsequently incubated for 24 hours at 37° C. with 5% CO2 and observed under a fluorescence microscope.

Additional experiments were performed, while the working distance was changed to 3 mm, the applied voltage covered a range of 2.5 kV to 3.5 kV, using a flow rate of 10 μl/min. A volume of 30 μl of plasmid suspension (500 μg eGFP per ml $H_2O$) corresponding to 15 μg of the plasmid was delivered towards the target T, wherein said water was diluted with 0%, 3 vol %, and 30 vol % ethanol.

C. Explanted Lung Tissue

As proof of the concept on regular lung tissue, slices of explanted lung (Fischer rats, F344, thickness 1-3 mm) were used. The tissue was placed within a 6-well plate with DMEM growth medium with 10% FCS (FIG. 7 left).

Before applying the electrospray, the growth medium was removed, and only the tissue remained. For electrospraying 50 μg/ml enhanced green fluorescent protein (eGFP) reporter gene suspended in distilled water was used.

The current was limited to 200 μA, while a potential of 4.5 kV was applied. At a flow rate of 100 μL/min a plasmid volume of 50 µL (2.5 µg plasmid) was delivered. The lung tissue was kept for 24 hours at 37° C., with 5% $CO_2$ subsequently.

Figure 7:
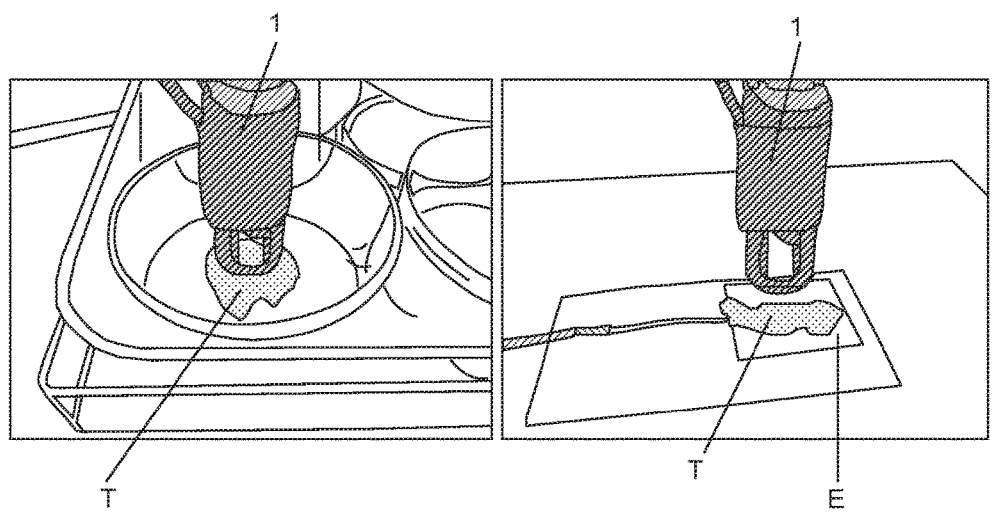
FIG. 7 shows an application of a device according to the invention on an explanted slice of lung tissue 1-3 mm thick (Adult Fischer rat, F344) within the well plate (left) and with an additional external electrode (right)

For comparison a second test was performed by applying an external electrode E to the tissue, disabling the integrated ground electrode 200 (FIG. 7 right).

Additional experiments were performed, while the working distance was changed to 3 mm, the applied voltage covered a range of 2.5 kV to 3.5 kV, using a flow rate of 10 µl/min. A volume of 30 µl of plasmid suspension (100 µg eGFP per ml $H_2O$) corresponding to 3 µg of the plasmid was delivered towards the target T. The water in the delivered media was additionally diluted with 3%; 9 vol % and 15 vol % ethanol.

Results

A. Cell Culture

Figure 8:
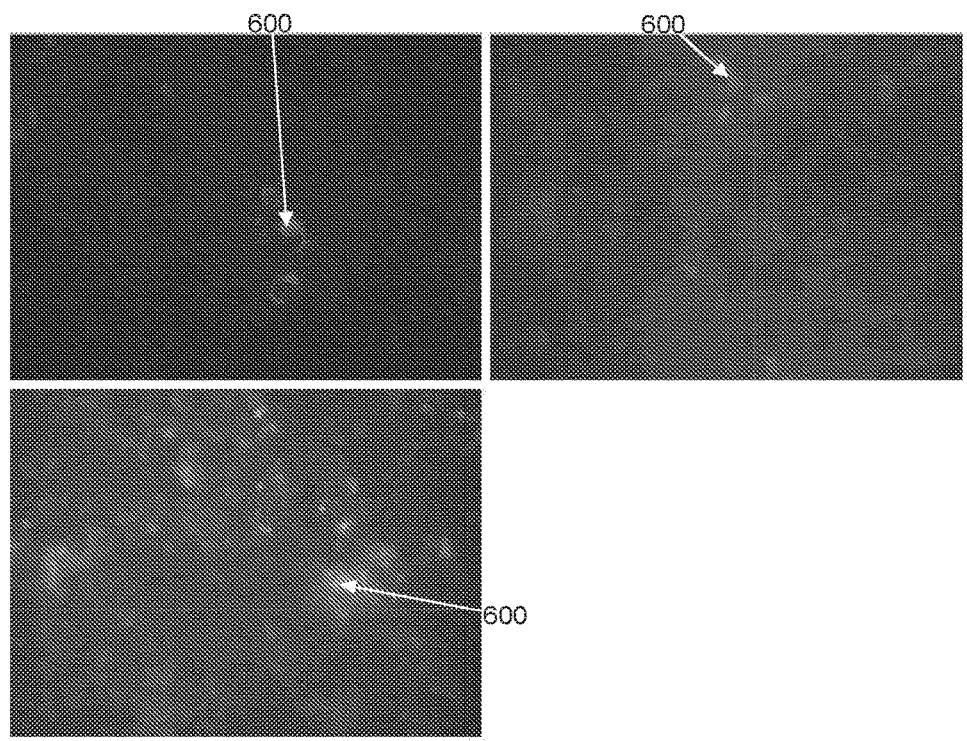
FIG. 8 shows fluorescence microscopic images of cell cultures, sprayed with GFP 5.0 kV (upper left), 5.5 kV (upper right) and 6.5 kV (lower left) after 24 hours incubation.
Figure 9:
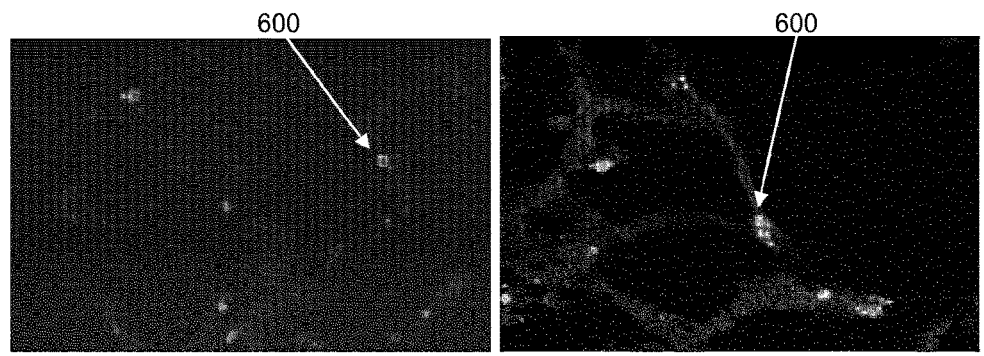
FIG. 9 shows fluorescence microscope images of lung tissue after 24 hours incubation at 37° C. GFP positive cells (green) can be observed using the device for electrospray (left) and using an additional external electrode (right)
Figure 10:
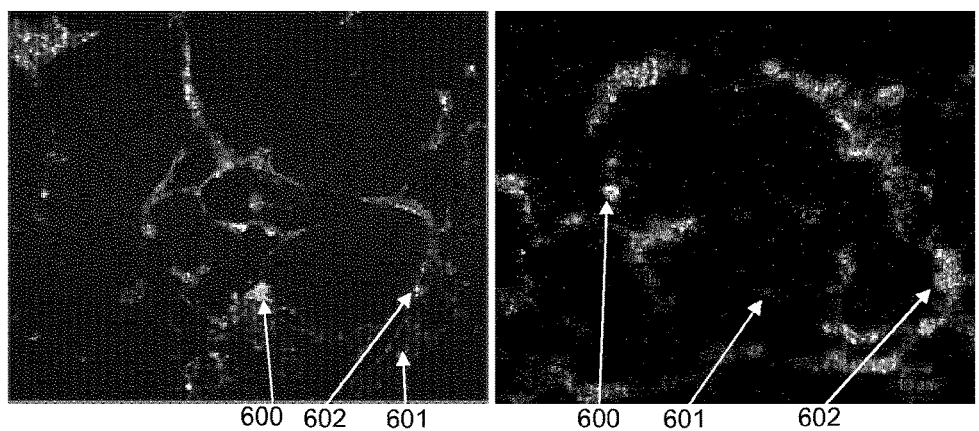
FIG. 10 shows fluorescence microscope images with transfected alveolar epithelial type II cells (orange), in contrast to non-transfected cells (red) and GFP (green) applied by an device according to the invention (left) and with an external electrode (right)

Using a potential from 5 to 6.5 kV the transfection of eGFP (green fluorescent protein plasmid) DNA can be observed using a fluorescence microscope. Shown in FIG. 8 the greenish spots 600 (one such spot is indicated by a white arrow as an example) represent single cells with transfected reporter gene. However, the transfection rate is quite poor, a transfection of GFP can clearly be observed. An improvement of transfection rate can be observed when increasing the potential.

The additional experiments provided an improved stability of the electrospray process. Transfection was observed in all three concentrations, wherein the highest concentration of green fluorescence was observed at a concentration of 3 vol %.

B. Ex-Vivo Lung Tissue

FIG. 9 (left) shows the fluorescence microscope images of the rat lung tissue, using an electrical potential of 4.5 kV. The greenish spots 600 (one such spot is indicated by a white arrow as an example) indicate the successful transfection of eGFP into the cells. The transfection rate is slightly higher as compared to the transfection of cell culture, even at lower applied potential. The fluorescence microscope image of the experiment with the external electrode E is shown in FIG. 9 (right).

To confirm the cell type transfected, a co-staining with surfactant protein C (SpC) antibody was performed. There were a number of double stained cells (eGFP: green spots 600 (one such spot is indicated by a white arrow as an example); SpC: red spots 601 (one such spot is indicated by a white arrow as an example), co-stained: orange spots 602 (one such spot is indicated by a white arrow as an example)), in the tissue slice as shown in FIG. 10. This proves that we are able to transduce the alveolar epithelial cells with this technique.

Furthermore, this concept can be also adopted to be used for minimally invasive approach in other organ systems too.

Fluorescence analysis of the additional experiments showed that increasing the ethanol concentration up to 15 vol % also increases the transfection efficiency of eGFP.

REFERENCES

[1] A. Gazdhar, P. Fachinger, C. van Leer, J. Pierog, M. Gugger, R. Friis, R. A. Schmid, and T. Geiser, "Gene transfer of hepatocyte growth factor by electroporation reduces bleomycin-induced lung fibrosis," Am J Physiol Lung Cell Mol Physiol, vol. 292 pp. L529-36 February 2007.

[2] D. Soden, M. Sadadcharam, J. Piggott, A. Morrissey, C. G. Collins, and G. C. O'Sullivan, "An endoscopic system for gene & drug delivery directly to intraluminal tissue," in 11$^{th}$ Mediterranean Conference on Medical and Biomedical Engineering and Computing 2007. vol. 16, R. Magjarevic, Ed.: Springer Berlin Heidelberg, 2007, pp. 628-628.

[3] Y. Okubo, K. Ikemoto, K. Koike, C. Tsutsui, I. Sakata, O. Takei, A. Adachi, and T. Sakai, "DNA Introduction into living cells by water droplet impact with an electrospray process," Angewandte Chemie, vol. 120, pp. 1451-1453, 2008.

[4] D.-R. Chen, C. Wendt, and D. Y. H. Pui, "A novel approach for introducing bio-materials into cells," Journal of Nanopartical Research, vol. 2, pp. 133-139, 2000.

The invention claimed is:

1. Device for spraying charged droplets of a liquid towards a target along a spraying direction, comprising:

a reservoir (10) for receiving the liquid (L), a first electrode (100) being arranged at an outlet (11) of said reservoir (10), a second electrode (200) forming a counter electrode to the first electrode (100) for accelerating said droplets (D) along the spraying direction (S), and a housing (30) holding the reservoir (10) as well as said electrodes (100, 200), wherein said housing (30) forms a spray chamber (31) extending along the spraying direction (S), wherein the reservoir (10) is connected to the spray chamber (31) via said outlet (11), and wherein the spray chamber (31) comprises an opening (32) facing said outlet (11) along the spraying direction (S) for electing the droplets (D) out of the spray chamber (31).

2. Device as claimed in claim 1, characterized in that an end region (200*a*) of the second electrode (200) is spaced apart from said outlet (11) along the spraying direction (S).

3. Device as claimed in claim 1, characterized in that the first electrode (100) comprises a tubular shape.

4. Device as claimed in claim 1, characterized in that the first electrode (100) extends into the spray chamber (31), wherein the first electrode (100) comprises a region (110) arranged on an inside (31*a*) of the spray chamber (31) extending along the spraying direction (S).

5. Device as claimed in claim 1, characterized in that the second electrode (200) is arranged at least in sections on a face side (10*a*) of the housing (30) delimiting said opening (32).

6. Device according to claim 1, characterized in that the spray chamber (31) comprises a plurality of lateral through-holes (H) for discharging liquid (L) accumulated in the spray chamber (31) out of the spray chamber (31).

7. Device as claimed in claim 1, characterized in that the second electrode (200) comprises a contact area (200*a*) being designed to contact said target (T) into which said liquid (L) is to be injected.

8. Device according to claim 1, characterized in that, the second electrode (200) comprises a circumferential free end region protruding from or out of the spray chamber (31), which free end region forms a contact area (200*a*) being designed to contact said target (T) into which said liquid (L) is to be infected.

9. Device as claimed in claim 1, characterized in that the second electrode (200) is arranged within the spray chamber (31).

10. Device as claimed in claim 1, characterized in that the second electrode (200) is arranged along the opening (32) of the spray chamber (31), wherein the second electrode (200) extends circumferentially along the opening (32) of the spray chamber (31).

11. Device according to claim 1, characterized in that the second electrode (200) or a free end region of the second electrode (200) protruding from the spray chamber (31) is designed to be expanded from a first state into a second state and contracted from the second state into the first state, wherein the second electrode (200) or said free end region comprises a larger diameter in the second state than in the first state, wherein the second electrode (200) or said free end portion is designed to be expanded from the first into the second state, when the second electrode (200) or said free end portion is pushed out of a working channel (501) of a tubular device (500), wherein the second electrode (200) or said free end portion is designed to be contracted from the second state into the first state, when the second electrode or said free end portion is pulled into a working channel (501) of a tubular device (500), wherein the second electrode (200) or said free end portion is made of or comprises a flexible, electrically conductive material, wherein the second electrode (200) or said free end portion is self-expanding or wherein the device (1) comprises an actuation means for expanding and/or contracting the second electrode (200) or said free end portion.

12. Device according to claim 1, characterized in that a connection (210) of the second electrode (200) to a voltage source (300) and/or the second electrode (200) is shielded from the first electrode (100) by a shielding (400), wherein said shielding (400) is connected to an electrical potential ranging from a potential of the first electrode (100) up to a potential below the potential of the second electrode (200).

13. Device according to claim 12, characterized in that a connection (210) of the second electrode (200) to the voltage source (300) comprises an inner conductor and an outer conductor surrounding the inner conductor, wherein the inner and the outer conductor are arranged coaxially with respect to each other, wherein the second electrode is connected to the respective inner conductor, while the respective outer conductor forming said shielding is connected to a different electrical potential in between the potential of the second electrode and the potential of the first electrode.

14. Device according to claim 12, characterized in that said shielding (400) is a cylindrical shielding which surrounds the first electrode (100) and is coaxially arranged with respect to the first electrode (100).

15. Device as claimed in claim 1, characterized in that the spray chamber (31) comprises at least one window (33).

16. Device according to claim 1, characterized in that the second electrode (200) comprises at least two separate electrode elements (200*b*-200*i*), wherein the device (1) is configured to switch the at least two electrode elements (200*b*-200*i*) so as to form a single counter electrode to the first electrode (100) in order to accelerate said droplets (D), wherein—after having accelerated said droplets (D)—the device (1) is further designed to apply a potential difference between the at least two electrode elements (200*b*-200*i*) for additional electroporation of the droplets (D) injected into the target.

17. Device according to claim 1, characterized by a voltage source (300) connected to the first and the second electrode (100, 200), which voltage source (300) is designed to generate a potential difference between the first electrode (100) and the second electrode (200) so as to accelerate said droplets (D) towards said target (T), wherein the voltage source (300) is designed to generate said potential difference as a continuous potential difference or a pulsed potential difference.

18. Device as claimed in claim 1, characterized in that the device (1) is configured to set the second electrode (200) on a potential different from ground and different from the first electrode (100), so as to enhance electroporation of the droplets (D) injected into the target (T) by increasing a membrane potential of said target (T).

19. Device as claimed in claim 1, characterized in that the device (1) comprises a plurality of second electrodes (200) arranged one after another along the spray chamber (31) along the spraying direction (S), wherein each two neighboring second electrodes (200) form a pair (P, P') of electrodes, wherein the first pair (P) is formed by the first electrode (100) and a neighboring second electrode (200) along the spraying direction (S), and wherein the device (1) is configured to generate a potential difference between said pairs (P, P') in a subsequent fashion along the spraying direction (S) starting from the first pair (P) so as to accelerate said droplets (D) between each pair (P, P') of electrodes along the spraying direction (S).

20. Device according to claim 1, characterized in that the device (1) is flexible, wherein the housing (30), the first electrode (100) and the second electrode (200) are made out of a flexible material, respectively.

21. Device according to claim 1, characterized in that the housing (30) or parts thereof are formed out of or are coated with a hydrophobic or super hydrophobic material, or contain nano- or microstructures so as to exhibit hydrophobic or super-hydrophobic properties.

22. System comprising a tubular device, in the form of an endoscope or a bronchoscope, and a device (1) according to claim 1, characterized in that the housing (30) is inserted into a working channel (501) of the tubular device (50) for arranging said housing (30) at the target (T).

23. Device for spraying charged droplets of a liquid towards a target along a spraying direction, comprising:
a reservoir (10) for receiving the liquid (L),
a first electrode (100) being arranged at an outlet (11) of said reservoir (10),
a second electrode (200) forming a counter electrode to the first electrode (100) for accelerating said droplets (D) along the spraying direction (S), and
a housing (30) holding the reservoir (10) as well as said electrodes (100, 200),
wherein the second electrode (200) comprises a contact area (200*a*) being designed to contact said target (T) into which said liquid (L) is to be injected, and wherein the second electrode (200) comprises a circumferential free end region protruding from or out of the spray chamber (31), which free end region forms said contact area (200*a*).

24. Device for spraying charged droplets of a liquid towards a target along a spraying direction, comprising:
a reservoir (10) for receiving the liquid (L),
a first electrode (100) being arranged at an outlet (11) of said reservoir (10),
a second electrode (200) forming a counter electrode to the first electrode (100) for accelerating said droplets (D) along the spraying direction (S), and
a housing (30) holding the reservoir (10) as well as said electrodes (100, 200),
wherein a connection (210) of the second electrode (200) to a voltage source (300) and/or the second electrode (200) is shielded from the first electrode (100) by a shielding (400), wherein said shielding (400) is connected to an electrical potential ranging from a potential of the first electrode (100) up to a potential below the potential of the second electrode (200).

* * * * *